United States Patent [19]

Regenass et al.

[11] Patent Number: 4,683,071
[45] Date of Patent: Jul. 28, 1987

[54] BENZOTRIAZOLE MIXTURES, PROCESSES FOR PRODUCING THEM, AND THEIR USE AS METAL PASSIVATORS

[76] Inventors: Franz Regenass, Oristalstrasse 45, 4410 Liestal; Peter C. Hamblin, Alemannenweg 12, 4112 Flüh, both of Switzerland

[21] Appl. No.: 788,690

[22] Filed: Oct. 18, 1985

Related U.S. Application Data

[63] Continuation of Ser. No. 466,823, Feb. 16, 1983, abandoned.

[30] Foreign Application Priority Data

Feb. 26, 1982 [CH] Switzerland .................. 1198/82

[51] Int. Cl.$^4$ ............... C07D 249/18; C10M 133/44
[52] U.S. Cl. ............................ 252/49.3; 252/49.5; 548/260
[58] Field of Search ................. 548/257, 260; 252/51.5 R, 49.3, 49.5

[56] References Cited

U.S. PATENT DOCUMENTS

| | | | |
|---|---|---|---|
| 3,413,227 | 11/1968 | Howard et al. | 252/51.5 R |
| 4,107,060 | 8/1978 | Schick et al. | 548/257 |
| 4,153,565 | 5/1979 | Braid et al. | 548/260 |
| 4,177,155 | 12/1979 | Popplewell | 548/260 |

FOREIGN PATENT DOCUMENTS

| | | | |
|---|---|---|---|
| 1948794 | 9/1969 | Fed. Rep. of Germany | 548/257 |
| 2530562 | 1/1977 | Fed. Rep. of Germany | 548/257 |
| 6033909 | 9/1976 | Japan | 548/257 |
| 1061904 | 3/1969 | United Kingdom | 252/49.5 |
| 1511593 | 5/1978 | United Kingdom | 548/257 |
| 1514359 | 6/1978 | United Kingdom | 252/49.5 |
| 653290 | 3/1979 | U.S.S.R. | 548/260 |

OTHER PUBLICATIONS

A. Katritzky, "Advances on Heterocyclic Chemistry", Academic Press, N.Y., (Supplement I), (1976), pp. 292–297.

Primary Examiner—Glenna M. Hendricks

[57] ABSTRACT

Mixtures of the compounds of the formulae I and II

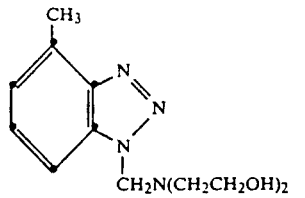

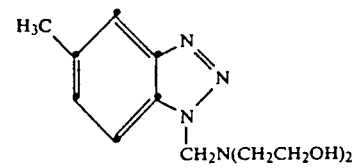

are metal passivators for functional fluids, such as hydraulic fluids and metal-working fluids in the form of aqueous polyglycol/polyglycol ether mixtures, glycol systems, oil-in-water and water-in-oil emulsions, as well as anti-freeze compositions based on glycol.

A process for producing mixtures of the said type is also described.

3 Claims, No Drawings

BENZOTRIAZOLE MIXTURES, PROCESSES FOR PRODUCING THEM, AND THEIR USE AS METAL PASSIVATORS

This is a continuation of application Ser. No. 466,823, filed on Feb. 16, 1983, now abandoned.

The invention relates to novel benzotriazole mixtures, to processes for producing them, and to their use as metal passivators for functional fluids.

It is known that organic compounds can be used as metal passivators, for example for copper or silver, in functional substrates, such as hydraulic fluids or in antifreeze solutions, for the protection of copper or silver objects against corrosion. Known compounds for this purpose are for example benzimidazole, benzothiazole and benzotriazole derivatives.

The last-mentioned compounds are described for example in the G.B. Pat. No. 1,061,904. Benzotriazole itself and many of the derivatives thereof have however in practice limited applicability on account of their poor solubility, especially in mineral oils.

Particularly advantageous for the functional fluids referred to above are metal passivators which have a high level of solubility, so that they can be rapidly and well dispersed in the substrates in which they are applied, a factor which ensures optimum protection for the metal objects concerned.

It has therefore been suggested in the U.S. Pat. No. 4,177,155 that the solubility of the said metal passivators, for example certain benzotriazole derivatives, in functional fluids, both those having an aqueous base and those having an oil base, may be improved by introduction of polar groups. As a result of their solid, oily or wax-like nature, compounds of this type are however not the most favourable. The oily or wax-like state of these products renders difficult their incorporation, or introduction in controlled amounts, into the substrates, whilst in the case of the solid products, a rapid dissolving of them is not possible, so that the mixing operation is impeded. Furthermore, dust is frequently formed on application, or on introduction in controlled amounts, of the solid products, which constitutes a further disadvantage.

The present invention thus relates to a mixture of the compounds of the formulae I and II

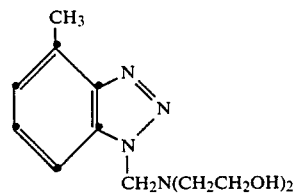

(I)

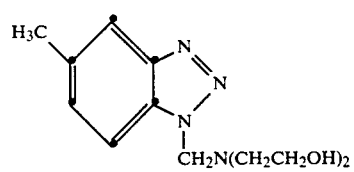

(II)

A preferred mixture is that consisting of 50 to 70 percent by weight of the compound of the formula I and 50 to 30 percent by weight of the compound of the formula II.

The mixtures according to the invention are fluids which have excellent solubility in water. They are distinguished by their rapid dispersibility and good distribution in the functional fluids having an aqueous base. It is moreover possible to incorporate them into the substrate by liquid-liquid introduction in controlled amounts.

Further subject matter of the present invention is a process for producing mixtures of the compounds of the formulae I and II, which process comprises reacting, in a manner known per se, a mixture of the compounds of the formulae III and IV

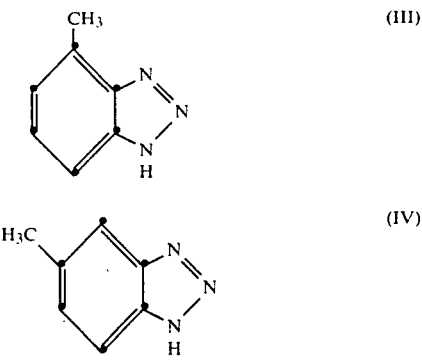

with formaldehyde and diethanolamine. Preferably used is a mixture of 50 to 70 percent by weight of the compound of the formula III and 50 to 30 percent by weight of the compound of the formula IV.

The required reactants of the formulae III and IV, or mixtures thereof, are known compounds, and can be produced for example by the process described in the G.B. Pat. No. 1,065,995.

The reagent formaldehyde is preferably used in the commercial form, for example as formalin (aqueous solution) or as paraformaldehyde.

The molar ratios of the mixture of 4- and 5-methylbenzotriazole to formaldehyde and to diethanolamine are preferably in approximately equimolar amounts.

The process of the invention is performed in particular by heating all the reactants together to an elevated temperature, for example to 50°-120° C. If desired, it is possible to firstly react formaldehyde and the appropriate mixture of 4- and 5-methylbenzotriazole with each other to give the corresponding N-methylol derivatives, before continuing the reaction with diethanolamine.

The process is preferably carried out without organic solvent. It can however be performed in the presence of an inert organic solvent. Suitable solvents for the purpose are for example: aliphatic and aromatic hydrocarbons, aliphatic alcohols and ketones, ethylene glycol monoether, polyethylene glycol monoether, ethylene glycol or propylene glycol.

A particular embodiment of the process is that whereby the reaction mixture obtained after completion of the reaction is filtered until clear, without any additional purification or possible separation of the solvent, and is then fed for further consumption directly into a container.

Mixtures of the compounds of the formulae I and II can be produced also by separate synthesis of the individual compounds of the formulae I and II from the compounds of the formulae III and IV, respectively, and subsequent mixing of the resulting compounds in the desired ratio to one another.

The mixtures of the compounds of the formulae I and II are Mannich bases which, by virtue of the tautomerism of triazole group and the presence of the methyl group in the benzene nucleus (positions 4 and 5), can exist in different isomeric forms (formulae V, VI and VII):

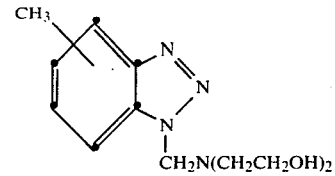
(V)

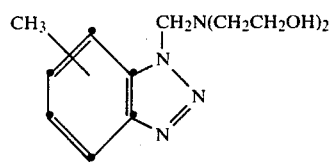
(VI)

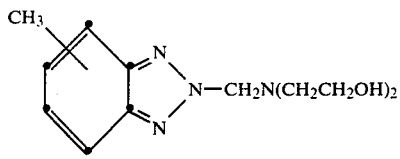
(VII)

It is known from the technical literature, for example Advances in Heterocyclic Chemistry, by A. Katritzky, or The Tautomerism of Heterocycles, Supplement 1, (1976), pp 292–297, that the so-called "1H form" is predominant in triazoles, so that therefore one of these isomeric "1H forms" V and VI has been selected for the description of the structures I to IV.

The mixtures of the compounds of the formulae I and II are viscous fluids at room temperature, and are therefore preferably used as aqueous solutions. Such solutions can be prepared by the addition of water in a ratio of mixture/$H_2O$ of 99:1 to 11:89, so that their viscosity can be optimumly adjusted according to requirements.

A particular embodiment of the invention is the use of aqueous solutions containing the mixtures of the compounds of the formulae I and II which are obtained directly after the reaction of the corresponding methylbenzotriazole mixtures with diethanolamine and aqueous formaldehyde, especially those containing between 15 and 30 percent by weight of water.

The mixtures of the compounds of the formulae I and II are excellent metal passivators which have a high level of solubility and which can be used in functional fluids. Examples of functional fluids are hydraulic fluids and metal-working fluids, for which the substances according to the invention are suitable, which fluids are based on aqueous polyglycol/polyglycol ether mixtures, glycol systems, oil-in-water and water-in-oil emulsions, as well as aqueous anti-freeze compositions having a glycol base.

Of particular interest are fluids which are mixed with water, for example anti-freeze, hydraulic and metal-working fluids.

Depending on the nature of the functional fluid, the composition of the invention preferably contains one or more co-additives. Examples of co-additives for such fluids are antioxidants, corrosion- and rust-inhibitors, further metal passivators, extreme pressure and anti-wear agents, biocides, buffers and foam inhibitors.

Examples of antioxidants are: 2,6-ditertiary butyl-p-cresol and phenyl-α-naphthylamine.

Examples of corrosion- and rust-inhibitors are: sodium nitrite, sodium benzoate, morpholine, amine soaps, for example triethanolamine-sebacate, triethanolamine phosphate, disodium hydrogen phosphate, disodium sebacate and arylsulfonamido-carboxylic acid ester.

Examples of further metal passivators are: benzotriazole and sodium mercaptobenzothiazole.

Examples of extreme pressure/antiwear additives are: chlorinated paraffin, sulfurised sperm oil, sulfurised olefins, ethoxylated half-esters and polyglycols.

Examples of buffers are: borax and triethanolamine.

Examples of biocides are: 2,4,5-trichlorophenol, sodium salt of 2,2'-dihydroxy-5,5'-dichlorodiphenyl methane and sodium salt of orthophenylphenol.

Examples of foam inhibitors are: silicones and polymethacrylates.

The mixtures of the compounds of the formulae I and II are added to the aforementioned functional fluids at a concentration of 0.001 to 5 percent by weight, relative to the total weight of the fluid.

The mixtures of the compounds of the formulae I and II according to the invention, and particularly the aqueous solutions thereof, can be readily incorporated, by simple liquid-liquid introduction in controlled amounts, into hydraulic fluids, metal-working fluids and anti-freeze compositions and are rapidly dissolved, especially with incorporation into the concentrates of functional fluids of the types mentioned, without heating being required. This results in a desirable saving in time and energy.

A further advantage of the said liquid mixtures is that they are easier to handle than the solid products. The liquid mixtures can be pumped, in the required quantity ratio, into the functional fluid substrates. The desired amount can be determined either by weighing or particularly by measurement by the volume.

Another advantage of the mixtures and solutions according to the invention is that they, in contrast to many solid products, cause no formation of dust when they are being introduced in controlled amounts or in some other way incorporated, which from the point of view of industrial hygiene is advantageous.

The following Examples further illustrate the invention.

EXAMPLE 1

27.85 parts by weight of diethanolamine and 35.25 parts by weight of a mixture consisting of about 65 percent by weight of 4-methylbenzotriazole and 35 percent by weight of 5-methylbenzotriazole are mixed together, and the mixture is heated to a temperature of 80°–25° C., in the course of which a clear solution is formed. After cooling of this solution to a temperature of 70° to 75° C., there are added, within about one half hour at this temperature, 21.5 parts by weight of formaldehyde as a 37% aqueous solution, the temperature being maintained by slight water cooling. The mixture is subsequently stirred for one hour at a temperature of 70°–75° C. The solution thus obtained is filtered clear without cooling and is poured directly into a container. The result is 84.6 parts of a solution containing a mixture of the compounds of the formulae I and II in the corresponding ratio of 65:35 (percent by weight) with respect to each other, and 18.4 parts by weight of water, in a virtually quantitative yield. The composition of this solution consists of about 78 percent by weight of the mixture of the compounds of the formulae I and II, and about 22 percent by weight of water. The kinematic viscosity of this solution is 45 mm²/sec (cSt) at 40° C.

The resulting solution can be used directly, without any intermediate isolation or purification, as a metal passivator in functional fluids. By virtue of its favourable viscosity, the solution can be incorporated into the aforementioned substrates, in a practical manner, by means of liquid-liquid introduction in controlled amounts, thus becoming rapidly mixed in and emulsified.

EXAMPLE 2

When the same reaction is carried out according to Example 1, except that the water is distilled off under reduced pressure from the reaction mixture after completion of the reaction, there are isolated 66.2 parts of a mixture of the compounds of the formulae I and II in practically quantitative yield. The resulting light-brown fluid has the following combustion analysis:

| calculated: | | found: | |
|---|---|---|---|
| C % | 57.6 | | 57.3 |
| H % | 7.2 | | 7.1 |
| N % | 22.4 | | 22.1 |

It contains about 65 percent by weight of the compound of the formula I and about 35 percent by weight of the compound of the formula II. This fluid can be used as a metal passivator in functional fluids, either directly or preferably after dilution with water.

EXAMPLE 3

Specimens of metals typical of those which are to be found in the cooling systems of internal combustion engines, for example in the motor cooling systems, are completely immersed in an aerated test solution for two weeks (336 hours) at 82° C., according to ASTM method D 1384-70. The corrosion preventive action of the solution is determined on the basis of the change in weight of the metal specimens.

The following formulation is used as the test solution:
67% by weight of water,
33% by weight of an ethylene glycol formulation consisting of:
  92.74 and 92.87% by weight, respectively, of ethylene glycol,
  2.9% by weight of triethanolamine,
  1.1% by weight of phosphoric acid,
  3.0% by weight of borax, and
  0.26 and 0.13% by weight, respectively, of the metal passivator according to Example 1.

The results are summarised in Table 1:

TABLE 1

| Metal passivator (percent by weight) | Changes in the weight of metal, expressed in mg/test specimen area | | | | |
|---|---|---|---|---|---|
| | Cu | brass | solder | steel | cast iron | Al |
| mixture according to Example 1 (0.26% at 78%, ≈ 0.2% at 100%) | −0.3 | +3.4 | −0.9 | −0.4 | −1.8 | −6.0 |
| mixture according to Example 1 (0.13% at 78%, ≈ 0.1% at 100%) | −0.9 | +3.9 | −1.3 | −0.4 | −3.2 | −5.5 |

A reduction in weight is denoted by the − sign, and an increase in weight is denoted by the + sign.

What is claimed is:

1. A mixture of the compounds of the formulae I and II

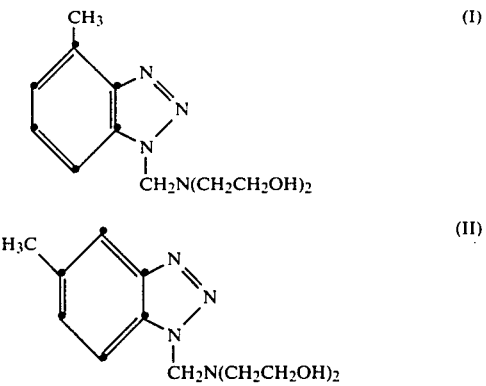

consisting of 50 to 70 percent by weight of the compound of formula I and 50 to 30 percent by weight of the compound of formula II.

2. A mixture according to claim 1 consisting of about 65 percent by weight of the compound of the formula I and about 35 percent by weight of the compound of the formula II.

3. A composition which consists, based on percent by weight of the total composition, of
 (a) 25 to 89 percent of water, and
 (b) 75 to 11 percent of a mixture of the compounds of the formulae I and II

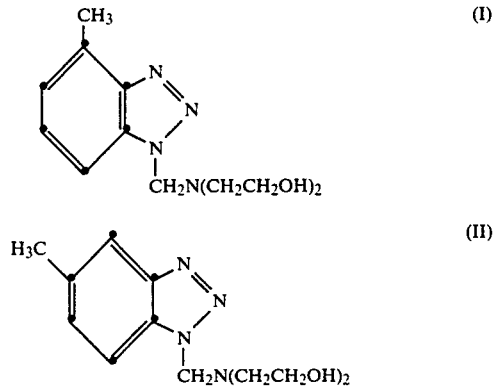

wherein component (b) consists of 50 to 70 percent by weight of the compound of formula I and 50 to 30 percent by weight of the compound of formula II.

* * * * *

UNITED STATES PATENT AND TRADEMARK OFFICE
CERTIFICATE OF CORRECTION

PATENT NO. : 4,683,071

DATED : JULY 28, 1987

INVENTOR(S) : FRANZ REGENASS, PETER C. HAMBLIN

It is certified that error appears in the above-identified patent and that said Letters Patent is hereby corrected as shown below:

On the cover page, Item [73] should be inserted to read -- Assignee: Ciba-Geigy Corporation, Ardsley, N.Y. --.

On the cover page, should read -- Attorney, Agent, or Firm- Luther A.R. Hall --.

Signed and Sealed this

Thirteenth Day of April, 1993

Attest:

STEPHEN G. KUNIN

Attesting Officer

Acting Commissioner of Patents and Trademarks